US010858302B2

United States Patent
Chen et al.

(10) Patent No.: US 10,858,302 B2
(45) Date of Patent: Dec. 8, 2020

(54) METHODS AND CATALYSTS FOR THE SELECTIVE PRODUCTION OF METHANOL FROM CARBON DIOXIDE AND HYDROGEN GAS FOR CHEMICAL SYNTHESIS AND GAS PURIFICATION

(71) Applicant: Catalytic Innovations, Inc., Fall River, MA (US)

(72) Inventors: Chi Chen, Beijing (CN); Juliet Khosrowabadi Kotyk, Providence, RI (US); Stafford Wheeler Sheehan, Tiverton, RI (US)

(73) Assignee: Catalytic Innovations, Inc., Fall River, MA (US)

( * ) Notice: Subject to any disclaimer, the term of this patent is extended or adjusted under 35 U.S.C. 154(b) by 0 days.

(21) Appl. No.: 16/012,749

(22) Filed: Jun. 19, 2018

(65) Prior Publication Data

US 2018/0362426 A1 Dec. 20, 2018

Related U.S. Application Data

(60) Provisional application No. 62/522,003, filed on Jun. 19, 2017.

(51) Int. Cl.
| | | |
|---|---|---|
| *C07C 29/157* | (2006.01) | |
| *B01J 23/89* | (2006.01) | |
| *B01J 23/80* | (2006.01) | |
| *B01J 37/08* | (2006.01) | |
| *B01J 35/00* | (2006.01) | |
| *B01J 37/34* | (2006.01) | |

(52) U.S. Cl.
CPC ............. *C07C 29/157* (2013.01); *B01J 23/80* (2013.01); *B01J 23/8926* (2013.01); *B01J 35/0013* (2013.01); *B01J 37/08* (2013.01); *B01J 37/343* (2013.01)

(58) Field of Classification Search
CPC ........ C07C 29/157; C07C 31/04; B01J 23/80; B01J 23/8926; B01J 35/0013; B01J 37/08; B01J 37/343; C10G 2/00; C10G 2/331
See application file for complete search history.

(56) References Cited

U.S. PATENT DOCUMENTS

| | | | | |
|---|---|---|---|---|
| 2014/0323600 A1* | 10/2014 | Jennings | ............... | C07C 29/151 518/713 |
| 2016/0121306 A1* | 5/2016 | Yu | ............................ | B01J 37/03 502/5 |

OTHER PUBLICATIONS

Cabrera et al., effect of Pd on Cu—Zn catalysts for the hydrogenation of carbon dioxide to methanol, (Catalysis Letter, vol. 79, No. 1-4, pp. 165-170, Apr. 2002).*
Bahruji et al., Pd/ZnO catalysts for direct carbon dioxide hydrogenation to methanol, (Journal of Catalysis 343 (2016), 133-146).*
Kulawska et al., copper/zinc catalysts in hydrogenation of carbon dioxide, (Chemical and process Engineering 2013, 34 (4), 479-496).*
Spencer, "The role of zinc oxide in Cu/ZnO catalysts for methanol synthesis and the water-gas shift reaction," Topics in Catalysis, 8:259-266 (1999).

* cited by examiner

*Primary Examiner* — Jafar F Parsa
(74) *Attorney, Agent, or Firm* — Foley Hoag LLP

(57) ABSTRACT

Catalysts and methods for the selective conversion of carbon dioxide and hydrogen into methanol using heat and high pressure in a hydrogenation reactor are disclosed. Key to this process are catalysts, which are comprised of multimetallic, aluminum oxide-supported nanoparticles. In some embodiments of the invention, the catalytic nanoparticles are made from mixtures of zinc and copper, or mixtures of palladium and copper, in different stoichiometric equivalents. In others, stoichiometric additives or dopants are added in order to improve the rate of product formation, improve selectivity, or allow for flow configurations. Methods for the use of these catalysts for the synthesis of methanol, and for the purification of $CO_2$, $H_2$, or CO gas streams by transforming contaminants into liquid methanol are also described.

20 Claims, 4 Drawing Sheets

METHODS AND CATALYSTS FOR THE SELECTIVE PRODUCTION OF METHANOL FROM CARBON DIOXIDE AND HYDROGEN GAS FOR CHEMICAL SYNTHESIS AND GAS PURIFICATION

CROSS-REFERENCE TO RELATED APPLICATIONS

This application claims the benefit of and priority to U.S. Ser. No. 62/522,003 filed Jun. 19, 2017 and which is incorporated by reference in its entirety.

STATEMENT REGARDING FEDERALLY SPONSORED RESEARCH OR DEVELOPMENT

Not applicable.

FIELD OF THE INVENTION

This invention is in the field of heterogeneous catalysis and hydrogenation. It focuses on methods of converting pressurized hydrogen gas and carbon dioxide, or hydrogen gas and carbon monoxide, into methanol over supported catalysts.

BACKGROUND OF THE INVENTION

Conversion of carbon dioxide into hydrocarbon chemicals using an external energy source is a fundamental process enabling life on our planet. In natural systems, plants use photosynthesis to convert carbon dioxide, water, and solar energy into chemical energy by creating sugars and other complex hydrocarbons. This process effectively stores the energy in absorbed photons from the sun in the chemical bonds of a carbon-based compound. This process has been supporting the Earth's ecosystem and balancing carbon dioxide concentration in our atmosphere for billions of years, having begun well before human beings evolved.

In the last century, human beings have harnessed byproducts of photosynthesis, such as fossil fuels, to provide the energy required for modern life. This behavior has released millions of tons of carbon dioxide into the Earth's atmosphere that had been previously sequestered into the fossil fuels by photosynthesis over the course of millions of years. To counteract this effect, researchers are increasingly exploring methods of converting carbon dioxide into useful chemicals. These methods include hydrogenation of carbon dioxide captured from the air using renewably-derived hydrogen gas.

Methanol, specifically, is one of the top ten commodity chemicals used by end users and as a starting material for other chemical products. End users include the automotive, construction and electronics industry. The chemical synthesis products of methanol include formaldehyde, acetic acid, and dimethyl ether. In 2015, the methanol market was a $101.4 billion industry. Methanol is a desirable alternative fuel source or energy carrier because is it suitable for flex fuel or fuel cell vehicles. Additionally, it is a liquid which makes transportation easier and safer than hydrogen gas. Methanol has a gasoline gallon equivalent (GGE) of 2, meaning it takes two gallons of methanol to equal the energy content of one gallon of gasoline.

Methanol is currently produced in a two-step process involving high temperatures and pressures that is energy intensive and non-renewable. Firstly, synthesis gas is produced from a costly high temperature break down of methane gas, a fossil fuel byproduct. Synthesis gas is a mixture of carbon monoxide (CO) and hydrogen ($H_2$). Secondly, synthesis gas is used over a catalyst bed at pressures of 5-10 MPa and temperature of 250° C. to generate methanol. Industrially the most common catalyst used for the preparation of methanol is copper oxide (CuO) and zinc oxide (ZnO) mixture supported on alumina ($Al_2O_3$). This overall reaction is embodied in the two balanced chemical equations shown below.

$$CH_4 + H_2O \rightarrow CO + 3H_2$$

$$CO + 2H_2 \rightarrow CH_3OH$$

There is increasing interest to produce alternative fuels, minimize the usage and effects of fossil fuel and its harmful emissions like carbon dioxide ($CO_2$). A carbon neutral cycle to produce methanol is possible through the hydrogenation of $CO_2$, also known as methanol steam reforming, as shown in the equation below. This process could upcycle carbon dioxide into a useful fuel.

$$CO_2 + 3H_2 \rightarrow CH_3OH + H_2O$$

Catalysts based on $CuO/ZnO/Al_2O_3$ are still active toward hydrogenation of $CO_2$ to generate methanol. However, typically a more active and expensive metal is needed. Palladium catalysts are commonly used because they have high activity like copper and are more stable. To date the best catalyst for methanol generation from hydrogenation of $CO_2$ is $Pd/Ga_2O_3$ with a yield of 6.4 $g_{methanol}/g_{catalyst}$ per hour. However, selectivity of Pd-based catalysts is usually low due to the reversed water gas shift (RWGS) reaction route shown in the equation below. It is very difficult to achieve all three important factors of catalysis: high conversions of $CO_2$, high yield/rate of methanol and high selectivity for methanol.

$$CO_2 + H_2 \rightarrow CO + H_2O$$

Recent advancements in catalyst development include a Pd/Zn core-shell catalyst with similar methanol yield to $Pd/Ga_2O_3$ and 70% selectivity using low pressure at 2 MPa. Indium oxides ($In_2O_3$) have also shown promise as highly selective hydrogenation catalysts for the conversion of $CO_2$ to methanol, but lack the requisite stability to be implemented industrially. Patented methods include gold on various metal oxides and use of Cr as a promotor in Pd/Cu systems.

The present invention discloses methods and their associated catalysts for production of methanol with high selectivity, achieving one of the three aforementioned goals, while optimizing rate and conversion efficiency.

SUMMARY OF THE INVENTION

It is an object of this invention to produce methanol from carbon dioxide and hydrogen gas (in some cases, renewably-derived hydrogen gas) using specific catalysts in a hydrogenation reactor. In certain aspects, the catalysts are bimetallic nanoparticles on a low cost, high surface area support, such as titanium dioxide. The catalysts described herein allow for exceptionally high selectivity for methanol, among liquid products effluent from the hydrogenation reaction.

In certain aspects, the hydrogenation reactor described herein is loaded with specific catalysts to accomplish selective methanol production and separation. Reactors include batch reactors, continuous stirred tank reactors, plug flow reactors, semibatch reactors, continuous reactors, laminar flow reactors, trickle-bed reactors, fluidized bed reactors, and any other reactor typically used for heterogeneous catalysis of gas to liquid transformations.

Mechanistically, the first step in carbon dioxide hydrogenation reactions is the formation of a carbon monoxide species on the catalyst surface. Therefore, it is an object of this invention to include highly selective hydrogenation of carbon monoxide to methanol as the primary liquid product, with high selectivity. This methodology can be used for purification of either carbon monoxide or hydrogen gas streams (i.e. to produce 100% pure $H_2$ or CO), by reacting a small amount of the product stream with the contaminant to produce a liquid hydrocarbon. The liquid is then easily separable from the gas stream.

Catalysts for this process include, but are not limited to, supported bimetallic and trimetallic nanoparticles. "Bimetallic" are compounds that contain stoichiometric amounts of two metal (alkali metal, alkaline earth metal, transition metal, lanthanide, actinide, and metalloid) elements. "Trimetallic" are compounds that contain stoichiometric amounts of three metal elements. "Tetrametallic" are compounds that contain stoichiometric amounts of four metal elements. "Nanoparticles" constitute small clusters of atoms ranging in size between 1 nanometer and 1000 nanometers. These nanoparticles are embedded on a support, so that high surface area and contact with reactants is realized. Supports, in this case, include but are not limited to titanium dioxide, carbon black, tin oxide, zinc oxide, magnesium oxide, zirconium oxide, niobium oxide, silicon oxides, and the like.

In certain aspects, specific formulations of catalysts for this process are compounds formed by reacting zinc- and copper-based precursors to produce bimetallic CuZn catalyst nanoparticles. These are supported on high surface area aluminum oxide, and packed or otherwise introduced to the hydrogenation reactor dry, in water, or some other solvent slurry. In the case of a flow reactor, these catalysts are loaded dry and mixed with an inert material, typically aluminum oxide. Dopants or ternary species, such as Rh, Ru, Fe, Na, K, Rb, or Cs can be introduced to help improve yield and selectivity of alcohols on catalysts such as these. These CuZn-based nanoparticles can be alloyed with elements to produce trimetallic, tetrametallic, or higher order nanoparticles.

In certain aspects, specific formulations of catalysts for this process are compounds formed by reacting palladium- and copper-based precursors to produce bimetallic $Pd_xCu$ catalyst nanoparticles. These are supported on high surface area titanium dioxide, and introduced to the hydrogenation reactor in water or other solvent slurry. Dopants or ternary species, such as Rh, Ru, and Fe, can be introduced to help improve yield and selectivity of methanol on catalysts such as these.

Peripheral systems for the hydrogenation reactor depend on the application. For example, for generation of methanol using only renewable energy resources, hydrogen gas can be supplied by an electrolyzer and carbon dioxide can be captured from the air. In another example, for purification of an industrial carbon dioxide or carbon monoxide stream possessing a small contaminant level of hydrogen gas, the contaminated carbon dioxide or carbon monoxide is fed into the reactor wherein the contaminant hydrogen is reacted with the carbon dioxide or carbon monoxide. This forms methanol using a small fraction of the product stream, which can be removed using a knock out drum, cold trap or any other process known to those skilled in the art that separates a room temperature liquid from a gas.

DETAILED DESCRIPTION OF THE INVENTION

Figure 1:
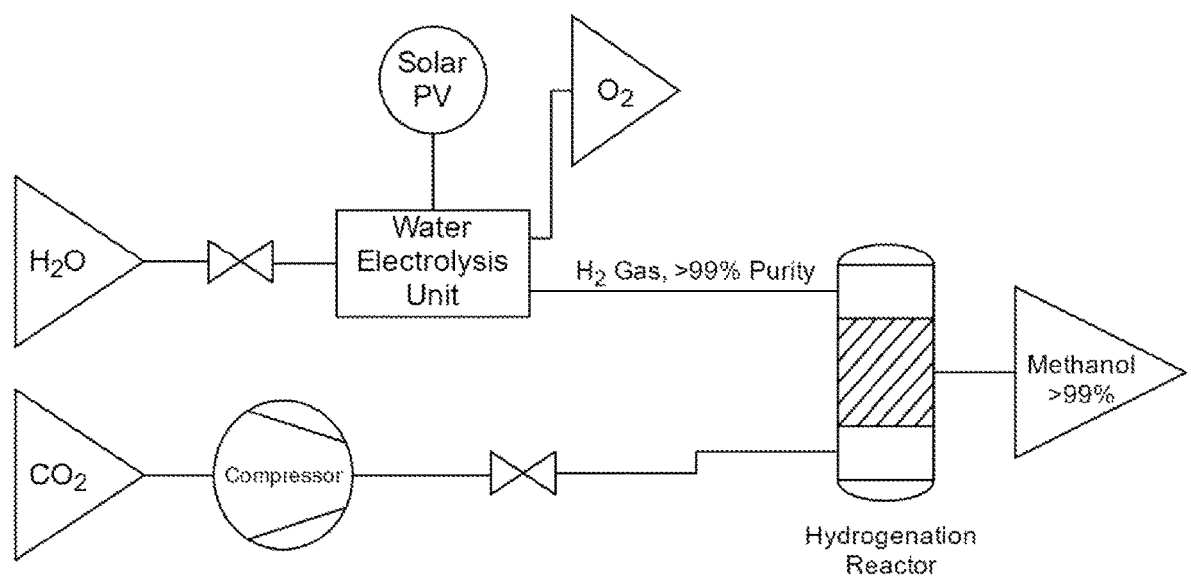
FIG. 1 shows a process flow diagram of one such system that can be used to perform the reaction, using an electrolyzer to supply hydrogen gas in a renewable manner.

The present application provides methods and catalyst formulations for the selective production of methanol by combining hydrogen gas with either carbon monoxide, carbon dioxide, or a mixture of both. This process is done at elevated temperatures and pressures in a pressure vessel (chemical reactor), so that yield and selectivity are optimized. Hydrogenation reactions such as are described herein use heat and pressure to react hydrogen gas with a low-energy carbon-based reactant, in this case carbon dioxide or carbon monoxide. This reaction is performed with a heterogeneous catalyst present inside the reactor, wherein the reactant products bind to the surface of the catalyst and are rearranged depending on the surface properties of the catalyst. The use of heat allows for C—H bond formation to overcome activation barriers present on the surface of the catalyst, while pressure improves the rate of reaction. Selectivity of the process is controlled by the catalyst, on which both heat and pressure have an effect.

Hydrogenation of carbon-based feedstocks with hydrogen gas has the advantage of being tunable by changing the catalyst present in the reactor, which requires minimal changes in overall reactor design. The present invention describes catalyst formulations, including but not limited to CuZn or $Pd_2Cu$ nanoparticles supported on aluminum oxide or titanium dioxide, that produce methanol with exceptionally high selectivity.

Due to the variety of products that can be produced by hydrogenation processes, selectivity is a critical metric in determining efficacy of a catalyst. The systems described herein, have selectivity for methanol production among liquid products of 75%, 80%, 85%, 90%, 95%, 99%, 99.9%, or higher.

Temperature and pressure are critical for tuning reaction conditions. In some embodiments of the present invention, the pressure vessel is able to withstand pressures up to 10 psi, 100 psi, 500 psi, 1000 psi, 1500 psi, 2000, psi, 3000 psi, 5000 psi, 10,000 psi, and higher. The ratio of pressures between hydrogen gas and carbon dioxide, for example, can also effect selectivity and yield of the process. In some embodiments, the partial pressure of carbon dioxide gas is 50 psi, 100 psi, 200 psi, 400 psi, 600 psi, 800 psi, or higher. The partial pressure of hydrogen is typically higher than that of carbon dioxide, and in some embodiments the partial pressure of hydrogen is 100 psi, 300 psi, 500 psi, 800 psi, 1000 psi, 2000 psi, 5000 psi, or higher. In some embodiments, the carbon dioxide is present in the liquid phase, in which the partial pressure of the liquid is higher than 860 psi at room temperature (25° C.). Pressures can include 1000 psi, 2000 psi, 5000 psi, or higher.

Temperatures that this reaction can be accomplished at using the catalysts described herein range from 100° C., 200° C., 400° C., 500° C., 700° C., and higher. Typical temperature ranges are between 150° C. and 350° C. When the reactant gases are introduced to a chemical reactor at these temperatures and the aforementioned pressures with the catalysts described in the present disclosure, methanol is produced with high selectivity among liquid products (>95%).

Catalysts for the process include, but are not limited to, CuZn or $Pd_2Cu$ nanoparticles or other high surface area materials with sizes ranging from 0.5 nm-10 nm that are embedded on a metal oxide support. In some cases, the support is comprised of approximately 15-30 nm average particle size of mixed phase (anatase and rutile) titania. In others, the support is aluminum oxide of high surface area. In others, the support is comprised of nanoparticles 10 nm, 20 nm, 50 nm, 100 nm, 500 nm, and higher. The support can be made using a variety of oxides, including but not limited to $Al_2O_3$, $ZrO_2$, $SnO_2$, $SiO_2$, $ZnO_2$, $TiO_2$, and others. It can also be comprised of mesoporous silica or a variety of carbon allotropes. Silicates, nitrides, fluorides, and other compounds can also be used as support materials.

Variations in catalyst formulation include ratios of Pd:Cu between 1:1, 2:1, 3:1, 5:1, and higher for Pd, and 1:2, 1:3, 1:5, and higher for Cu. In some cases, a third and/or fourth compound is introduced to the particles, which can include one or more of the following: Pt, Ru, Rh, Jr, Au, Ni, Co, Li, Na, Fe, Zn, K, Se, Ca, Mg, Mn, Sr, Ba, Ag, Sm, La, Ti, V, Zr, Nb, Mo, Re, Sn, Ce, or other elements. Substitution of Pd or Cu with other elements in its group or with similar valence configurations are also methods of producing catalysts as described in this invention.

Variations in catalyst formulation include ratios of Zn:Cu between 1:1, 2:1, 3:1, 5:1, and higher for Zn, and 1:2, 1:3, 1:5, and higher for Cu. In some cases, a third and/or fourth compound is introduced to the particles, which can include one or more of the following: Pt, Ru, Rh, Ir, Au, Ni, Co, Li, Na, Fe, Pd, K, Se, Ca, Mg, Mn, Sr, Ba, Ag, Sm, La, Ti, V, Zr, Nb, Mo, Re, Sn, Ce, or other elements. Substitution of Zn or Cu with other elements in its group or with similar valence configurations are also methods of producing catalysts as described in this invention.

Synthetic methods for the production of these catalytic nanoparticles and mesoporous materials include synthesis from nitrate, chloride, fluoride, halide, acetylacetonate, acetate, amine, carboxylic acid, and other chemical precursors. Synthetic methods can include, but are not limited to, ultrasonication, thermal annealing, sol-gel methods, freezing, wet/dry impregnation, and other methods.

Figure 2:
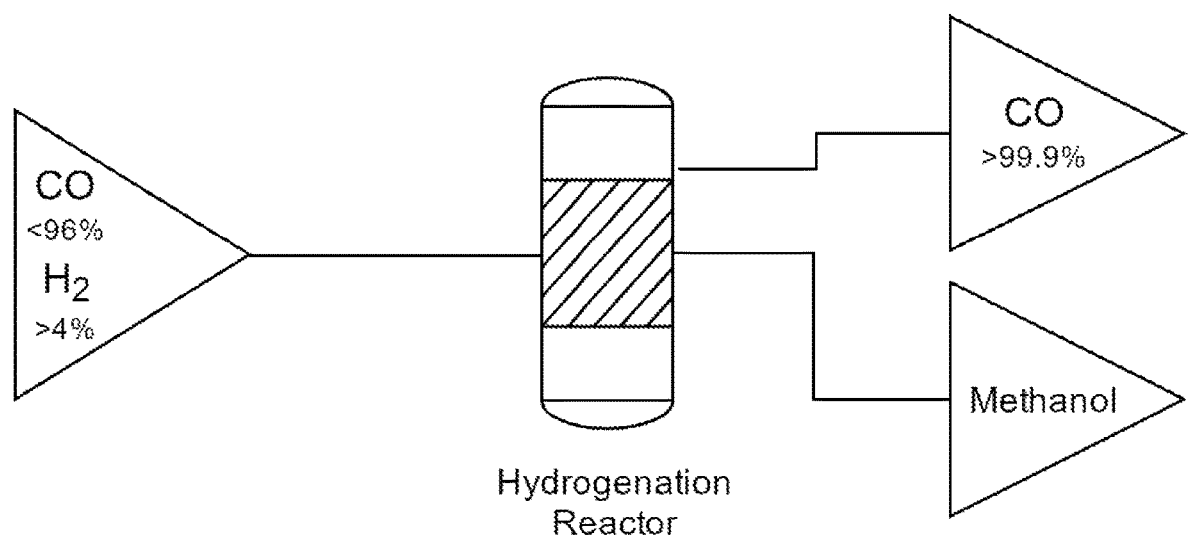
FIG. 2 shows a process flow diagram of another system that can be used to purify $H_2$-contaminated CO gas by selectively reacting the $H_2$ with CO and separating the liquid product.
Figure 3:
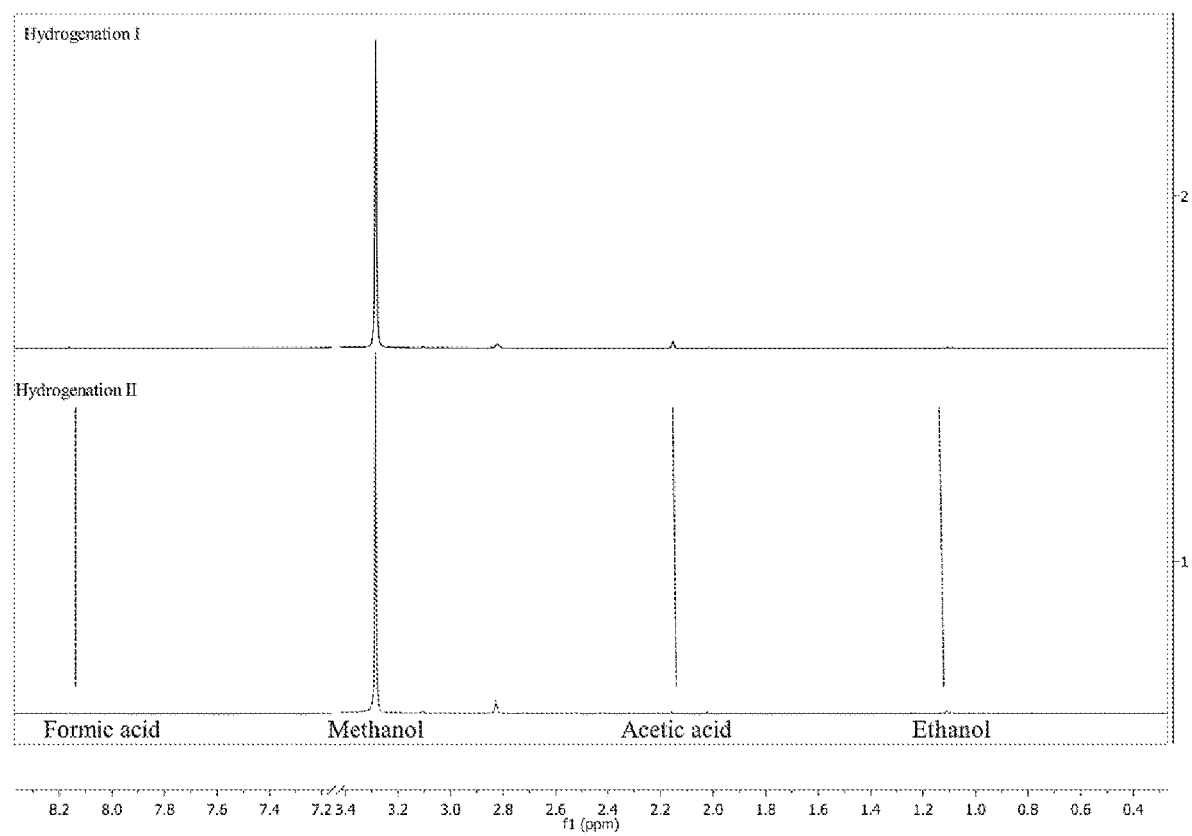
FIG. 3 shows $^1H$ nuclear magnetic resonance (NMR) spectra of the reaction product from hydrogenation experiments performed with water as a solvent, from two independent trials to demonstrate the reproducibility of these methods, both displaying a prominent methanol signal at 3.3 ppm, with a maleic acid internal standard (3.4 ppm).
Figure 4:
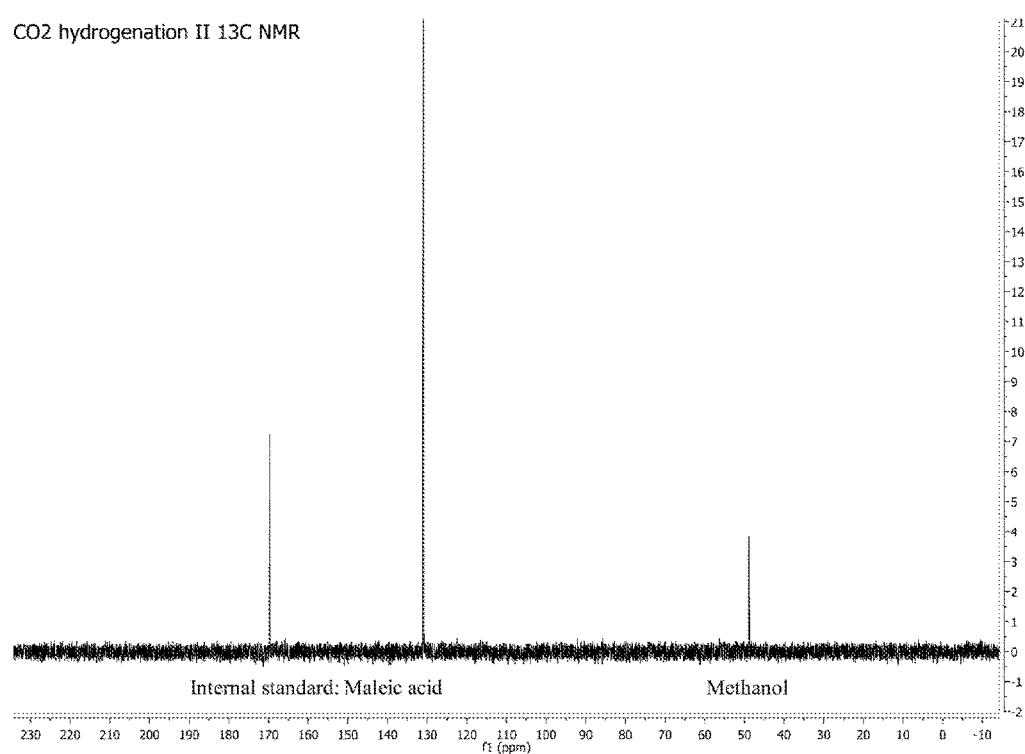
FIG. 4 shows $^{13}C$ NMR spectra of the reaction product, showing methanol as the only detected product.

The reactor can be a standalone system for chemical synthesis, or incorporated into a renewable chemical synthesis scheme (FIG. 1), or incorporated into a gas purification scheme (FIG. 2). In either case, the hydrogenation of a carbon-based feedstock gas that includes carbon dioxide, carbon monoxide, or a mixture of the two, with hydrogen gas, is accomplished using the catalytic process described herein.

Example 1

Preparation of Catalysts for Selective Methanol Production

Palladium(II) acetylacetonate (10 mg), copper(II) acetylacetonate (6.7 mg), ferric chloride hexahydrate (5.4 mg), ascorbic acid (35.6 mg) and oleylamine (5 mL) were added into a glass vial. The mixture was ultrasonicated for 2 hours. It is then heated in oven at 160° C. for 5 hours and 180° C. for 3 hours. The nanoparticles were collected by centrifugation and washed three times with mixture of cyclohexane and ethanol (1:1). The nanoparticles were then loaded to P25 Titanium Dioxide support (21 nm particle size) by stirring together in chloroform solution for 3 hours. The supported catalyst was then separated by centrifugation and washed with acetone three times to result in a white-colored powder. The product was thermally annealed in air at 300° C. for 1 hour and then in 5% $H_2/N_2$ at 300° C. for 1 hour, resulting in a dark blue/black powder.

Example 2

Production of Methanol by Carbon Dioxide Hydrogenation on a $Pd_2Cu$ Catalyst

For Hydrogenation Run I, 5.4 mg of supported catalyst synthesized as described in Example 1 was charged along with 5 mL of DI water into a Teflon liner in a 100 mL continuously stirred batch reactor. The reactor was then pressurized with carbon dioxide (100 psi) and hydrogen (364 psi). The reaction was performed with mechanic stirring at 200° C. for 5 hours before cooling down to room temperature. The system was then vented and the liquid products were filtered through Celite. The liquid mixture was analyzed with NMR spectroscopy with maleic acid as internal standard, and it was found to have generated 0.5 mmol (0.02 g) methanol. It produced other compounds in smaller ratios, specifically ethanol:methanol:formic acid: acetic acid=1:63:0.2:0.3 indicating 63 times more methanol than other products.

For Hydrogenation Run II, 13.5 mg of supported catalyst was charged along with 10 mL of DI water into a Teflon liner in a 100 mL continuously stirred batch reactor. The reactor was then pressurized with carbon dioxide (140 psi) and hydrogen (390 psi). The reaction was performed with mechanic stirring at 200° C. for 5 hours before cooling down to room temperature. The system was then vented and the liquid products were filtered through Celite. The liquid mixture was analyzed by NMR spectroscopy with maleic acid as internal standard, and it was found to have generated 1.6 mmol (0.05 g) of methanol. It produced other compounds in smaller ratios, specifically ethanol:methanol:formic acid:acetic acid=1:176:2:5.

TABLE 1

Reaction Conditions and Results for Carbon Dioxide Hydrogenation to Methanol

|  | Hydrogenation Run I | Hydrogenation Run II |
|---|---|---|
| Pressure of $CO_2$ (psi) | 100 | 140 |
| Pressure of $H_2$ (psi) | 364 | 390 |
| Temperature (° C.) | 200 | 200 |
| Selectivity | 98% | 96% |
| $CO_2$ conversion to methanol | 2% | 5% |
| Yield of methanol (g · $g_{cat}^{-1}$ · $h^{-1}$) | 48 | 63 |

All publications and patents mentioned are incorporated by reference in their entirety by reference. In case of conflict, the present application, including any definitions noted herein, will control.

We claim:

1. A method for the conversion of a gaseous stream of a carbon-based reactant and a hydrogen gas into methanol, the method comprising:
    providing a reaction vessel comprising a catalyst supported on a metal oxide, the catalyst comprising nanoparticles comprising:
    a) CuZn alloyed with a third transition metal; or
    b) $Pd_2Cu$ alloyed with a third transition metal;
    feeding the carbon-based reactant and the hydrogen gas into the reaction vessel; and
    heating said reaction vessel, thereby generating methanol.

2. The method of claim 1, wherein the ratio of zinc to copper in the catalyst is approximately 1:1.

3. The method of claim 1, wherein a partial pressure of the carbon-based reactant is between 80 psi and 500 psi.

4. The method of claim 2, wherein a partial pressure of hydrogen is between 250 psi and 1000 psi.

5. The method of claim 1, wherein the transition metal is selected from Pt, Ru, Rh, Ir, Au, Ni, Co, Fe, Zn, Mn, Ag, Ti, V, Zr, Nb, Mo, Re, or a combination thereof.

6. The method of claim 1, wherein the catalyst further comprises stoichiometric amounts of, or is doped with Li, Na, K, Rb, Cs, Se, Ca, Mg, Sr, Ba, Sm, La, Sn, Ce, or a combination thereof.

7. The method of claim 1, wherein the hydrogen gas supplied to the reaction vessel is made by water electrolysis.

8. The method of claim 1, wherein the selectivity of the catalyst for methanol over other liquid products is greater than 90%.

9. The method of claim 1, wherein the reaction vessel comprises a fixed bed reactor.

10. The method of claim 1, wherein the reaction vessel comprises a fluidized bed reactor.

11. The method of claim 1, wherein the carbon-based reactant comprises greater than 90% CO and the hydrogen gas comprises less than 10% $H_2$.

12. The method of claim 11, wherein the carbon-based reactant comprises greater than 95% CO and the hydrogen gas comprises less than 5% $H_2$.

13. The method of claim 1, wherein the carbon-based reactant comprises greater than 90% $CO_2$ and the hydrogen gas comprises less than 10% $H_2$.

14. The method of claim 1, wherein the carbon-based reactant comprises greater than 95% CO and the hydrogen gas comprises less than 5% $H_2$.

15. The method of claim 1, wherein the hydrogen gas comprises greater than 90% $H_2$ and the carbon-based reactant comprises less than 10% CO.

16. The method of claim 15, wherein the hydrogen gas comprises greater than 95% $H_2$ and the carbon-based reactant comprises less than 5% CO.

17. The method of claim 16, wherein the hydrogen gas comprises greater than 99% $H_2$ and the carbon-based reactant comprises less than 1% CO.

18. The method of claim 1, wherein the metal oxide is selected from the group consisting of: $Al_2O_3$, $ZrO_2$, $SnO_2$, $SiO_2$, ZnO, and $TiO_2$.

19. The method of claim 1, wherein the carbon-based reactant and the hydrogen gas are fed to the reaction vessel at a pressure greater than 300 pounds per square inch (psi) but less than 1500 psi.

20. The method of claim 1, wherein the reaction vessel is heated to a temperature between 150° C. and 350° C.

* * * * *